US009285036B2

(12) United States Patent
Cook

(10) Patent No.: US 9,285,036 B2
(45) Date of Patent: Mar. 15, 2016

(54) HIGH PRESSURE AND TEMPERATURE VALVE

(71) Applicant: Colin Donald Cook, Bedfordshire (GB)

(72) Inventor: Colin Donald Cook, Bedfordshire (GB)

(73) Assignee: Gates Corporation, Denver, CO (US)

( * ) Notice: Subject to any disclaimer, the term of this patent is extended or adjusted under 35 U.S.C. 154(b) by 454 days.

(21) Appl. No.: 13/721,489

(22) Filed: Dec. 20, 2012

(65) Prior Publication Data

US 2013/0152672 A1   Jun. 20, 2013

Related U.S. Application Data

(60) Provisional application No. 61/577,772, filed on Dec. 20, 2011.

(51) Int. Cl.
*F16K 15/00* (2006.01)
*F16K 1/32* (2006.01)
*F16K 11/07* (2006.01)
*G01M 3/02* (2006.01)

(52) U.S. Cl.
CPC . *F16K 1/32* (2013.01); *F16K 11/07* (2013.01); *G01M 3/02* (2013.01)

(58) Field of Classification Search
CPC .................................................. F16K 31/122
USPC ............ 251/5, 14, 28, 129.03, 175, 213, 226, 251/227, 238–246, 319–325; 137/605, 606
See application file for complete search history.

(56) References Cited

U.S. PATENT DOCUMENTS

| 4,026,322 | A | * | 5/1977 | Thomas | F04B 53/1022 137/512 |
| 5,092,744 | A | | 3/1992 | Boers et al. | |
| 5,339,677 | A | | 8/1994 | Haug | |
| 5,879,137 | A | | 3/1999 | Yie | |
| 5,881,768 | A | * | 3/1999 | Bezos | B60T 13/665 137/602 |
| 6,050,081 | A | * | 4/2000 | Jansen | F02C 7/232 137/112 |
| 6,591,201 | B1 | | 7/2003 | Hyde | |
| 2005/0160716 | A1 | * | 7/2005 | Jansen | F01D 25/12 60/39.094 |
| 2006/0042701 | A1 | * | 3/2006 | Jansen | F16K 1/38 137/606 |

FOREIGN PATENT DOCUMENTS

| CN | 2672643 Y | 1/2005 |
| CN | 201508303 U | 6/2010 |
| CN | 201615247 U | 10/2010 |
| CN | 102121846 A | 7/2011 |
| DE | 1107039 B | 5/1961 |
| WO | 2004111509 A1 | 12/2004 |

OTHER PUBLICATIONS

State Intellectual Property Office of the People's Republic of China, Notification of the First Office Action, Mailing date May 6, 2015, Application No. 201280062795.8, pp. 6, Search Report, Related Patent Documents.
The International Bureau of WIPO, International Preliminary Report on Patentability, Issuance of the report Jun. 24, 2014.
State Intellectual Property Office of the People's Republic of China, Notification of the Second Office Action; Date of Mailing: Dec. 21, 2015.

* cited by examiner

*Primary Examiner* — Hezron E Williams
*Assistant Examiner* — Hoang Nguyen
(74) *Attorney, Agent, or Firm* — Jeffrey A. Thurnau, Esq.; Paul N. Dunlap, Esq.

(57) ABSTRACT

The present disclosure is directed to systems and methods which provide a seal-less high temperature and pressure valve for use in many applications.

3 Claims, 4 Drawing Sheets

HIGH PRESSURE AND TEMPERATURE VALVE

REFERENCE TO RELATED APPLICATIONS

This application claims priority from U.S. provisional patent application No. 61/577,772 filed Dec. 20, 2011.

BACKGROUND

This disclosure relates generally to hose testers, more particularly to high pressure and temperature hose testers, and specifically to a high pressure and temperature valve used for cycling high pressure and temperature fluids to a hose(s) for testing

SUMMARY

The present disclosure is directed to systems and methods which provide a seal-less high temperature and pressure valve for use in many applications.

The foregoing has outlined rather broadly the features and technical advantages of the present disclosure in order that the detailed description of the disclosure that follows may be better understood. Additional features and advantages of the disclosure will be described hereinafter which form the subject of the claims of the disclosure. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope of the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

http://www.interlaken.com/pressure-systems/
http://www.brighthubengineering.com/hydraulics-civil-engineering/43882-learn-about-hydraulic-intensifiers/#

BRIEF DESCRIPTION OF THE DRAWINGS

The accompanying drawings, which are incorporated in and form part of the specification in which like numerals designate like parts, illustrate embodiments of the present disclosure and together with the description, serve to explain the principles of the disclosure. In the drawings.

DETAILED DESCRIPTION

Figure 1:
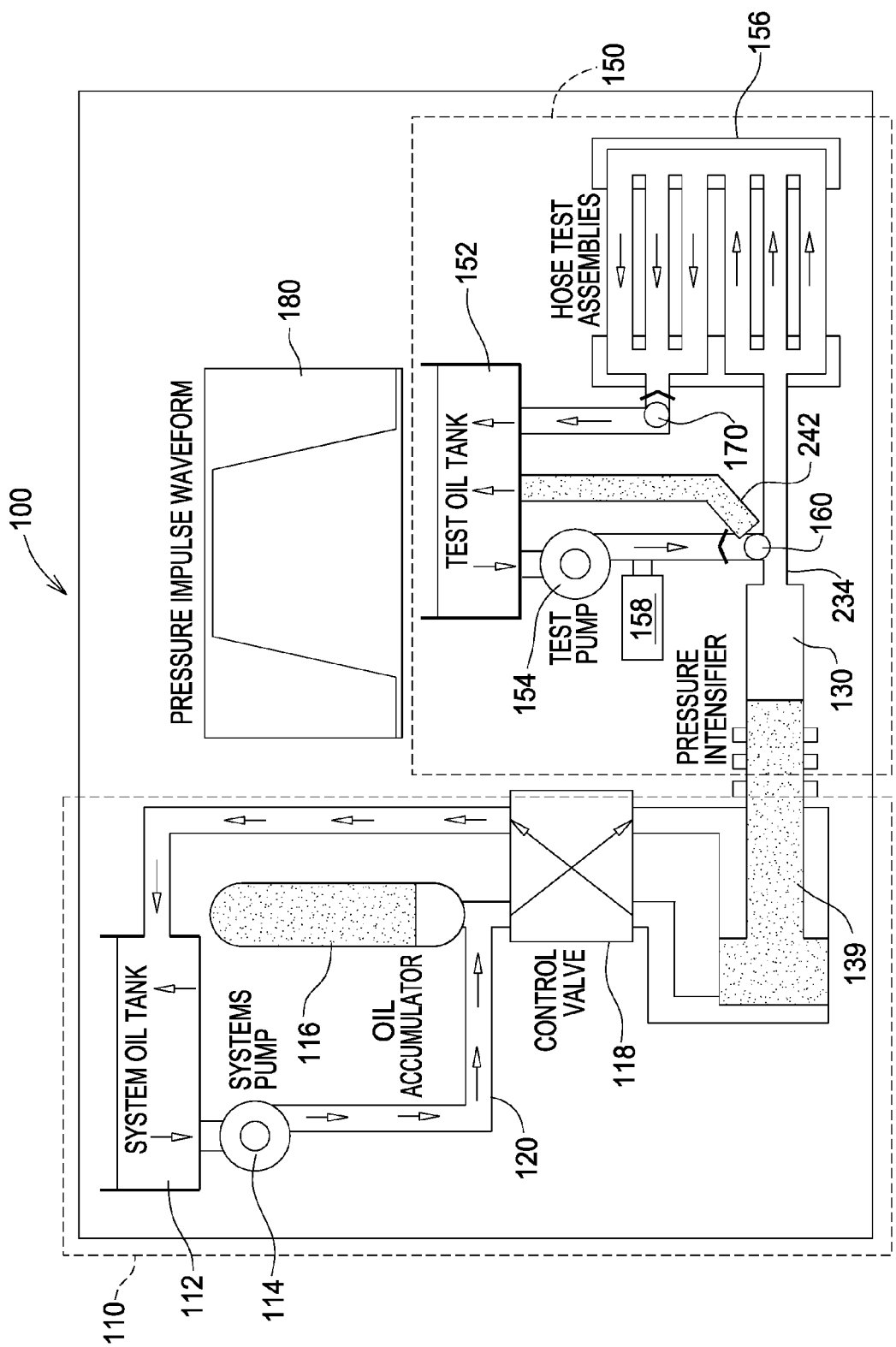
FIG. 1 is a block diagram of a hose tester at a low pressure state, according to an embodiment of the disclosure.

FIG. 1 shows a block diagram of a hose test system 100 during a low pressure cycle, as indicated by pressure waveform 180, according to an embodiment. Generally the right side of the pressure wave window indicates which portion of the cycle the system 100 is in. System 100 may include a control system 110, and a test system 150. The control system 110 may be configured to control the operation of an intensifier 130.

Control system 110 may include a system oil tank 112, a system pump 114, an accumulator 116, a control valve 118, and interconnecting piping 120.

System oil tank 112 may function as a storage tank for the oil/liquid used with control system 110. System pump 114 may be operatively coupled to system oil tank 112 and piping 120 to circulate oil throughout the system 110. System pump 114 may also function to fill accumulator 116.

Accumulator may be used to store oil to actuate intensifier 130. System pump 114 may not be able to pump enough oil fast enough to actuate intensifier 130. Thus accumulator 116 is needed to provide the pressure characteristics needed for proper operation of the intensifier 130. Control valve 118 may function to direct the flow of oil to and from intensifier 130 and accumulator 116, as well as throughout the system 110.

In the low pressure embodiment shown in FIG. 1, as indicated by pressure waveform 180, oil may flow to intensifier 130 to move piston 139 back to a non-actuated position. In this position control valve 118 may also direct flow of oil throughout the system 110, and to and from system oil tank 112. During this low pressure phase, accumulator 116 may also be filled to prepare for the next high pressure stage of operation. Furthermore, oil may be generally circulated throughout the system 110.

According to embodiments, test system 150 may include a test oil tank 152, test pump 154, hose test assembly 156 and oil temperature control system 158. Test system 150 may also include an inlet high pressure valve 160 and an outlet high pressure valve 170.

Test oil tank 152 may function as a storage tank for the test oil/liquid used with test system 150. Test pump 154 may be operatively coupled to system oil tank 152 and piping to circulate test oil throughout the test system 150.

Oil temperature control system 158 may function to keep the temperature of the test oil within an acceptable range. Oil temperature control system 158 may include heaters and coolers as well as heat exchangers and/or any other systems to maintain the test oil in an acceptable range.

In the low pressure embodiment of FIG. 1, test pump 154 may move oil through inlet valve 160 and through hose test assemblies 156. This may cause oil to go through outlet valve 170 and back to test oil tank 152. When inlet valve 160 allows oil to flow to hose test assembly 156, it may not allow flow of oil directly back into test oil tank 152 through pipe 242. Test assembly 156 may include manifolds with one or more hose coupled in a test manner.

Valves 160 and 170 may be capable of operating at 700 bar and 150 degrees Celsius for millions of cycles. The intensifier may be described in more detail in co-pending and co-filed patent application entitled "HOSE TESTER INTENSIFIER," having Ser. No. 61/577,742.

The control system 110 and test system 150 will not allow for comingling of oil. The test system 150 may have pressures exceeding 700 bar, while the control system 110 may be in the range of 8 bar. Furthermore, the test system 150 may include oil at temperatures exceeding 150 degrees Celsius, while the control system 110 may have oil reaching 50 degrees Celsius. In an embodiment, test system 150 may operate around 700 bar, and may also operate at 212, 250, and 300 degrees Fahrenheit, or any other temperature.

In this embodiment of the low pressure portion of the cycle, system pump 114 moves the piston 139 into a non-actuates position, and charges or fills accumulator 116. Valves 160 and 170 are in an "open" position, thereby allowing oil to flow through the hose test assembly 156.

Figure 2:
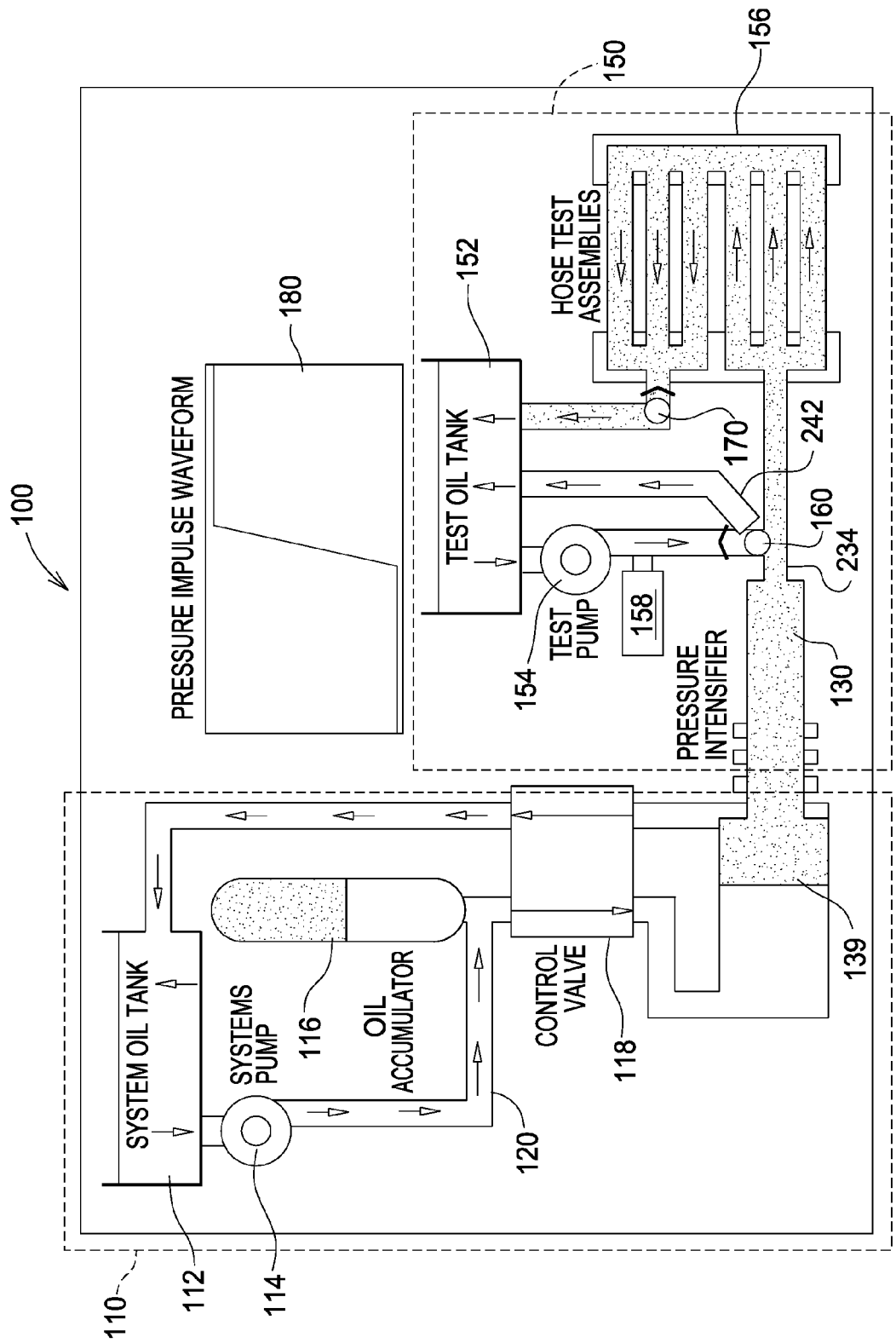
FIG. 2 is a block diagram of a hose tester at a high pressure state, according to an embodiment of the disclosure.

FIG. 2 shows an embodiment of a hose testing system 100, during a high pressure portion of operation. As seen generally at the right side of the pressure waveform 180, the pressure is generally at a high point of operation.

In this embodiment, control system 110 may operate in the following manner. Control valve 118 changes position to allow oil form the accumulator 116 which may cause piston 139 to move.

The test system 150 will operate as follows. Inlet valve 160 and outlet valve 170 will close. Since piston 139 of intensifier 130 is moving generally forward (to the right in the Figure), this will cause the pressure in test assembly 156 to rise relatively rapidly. Test pump 154 may continue to operate and cycle oil through inlet valve 160, back into test oil tank 152 as shown.

Once the acceptable high pressure is achieved within test system 150, the pressure may be held relatively constant for a period of time via piston 139. System pump 114 may then charge accumulator 116. This period of time may typically be about 0.4 seconds, with the total cycle time of about 1.0 seconds. However, other pressure cycle and total cycle times may be used without straying from the concepts disclosed herein.

Acceptable high pressure may be from about 250-800 bar. In embodiments, the acceptable high pressure may be generally about 700 bar. It will be appreciated that this is an embodiment of pressures and temperatures, many, many other temperatures and pressures may be tested, along with many different hoses, with test system 100.

Once an acceptable period of time has passed at the acceptable high pressure, valves 160 and 170 may open, control valve 118 may change positions, and a low pressure portion of the cycle may start. Control system 110 would then move piston 139 back to reduce pressure (to the left in the Figure), as will opening of valves 160 and 170. The cycle may then start over again.

Intensifier 130 may be made of carbon steel, and flash chromed to harden and to stop abrasion. This chroming may have the added benefit of allowing seals with the intensifier 130 to last longer, thereby decreasing maintenance time and cost. Furthermore, intensifier 130 made be formed from a single block of carbon steel which may allow for less failures and thereby reduced maintenance time and cost. Yet further, intensifier 130 may be water or other liquid cooled to increase life, thereby reducing maintenance time and cost.

Figure 3:
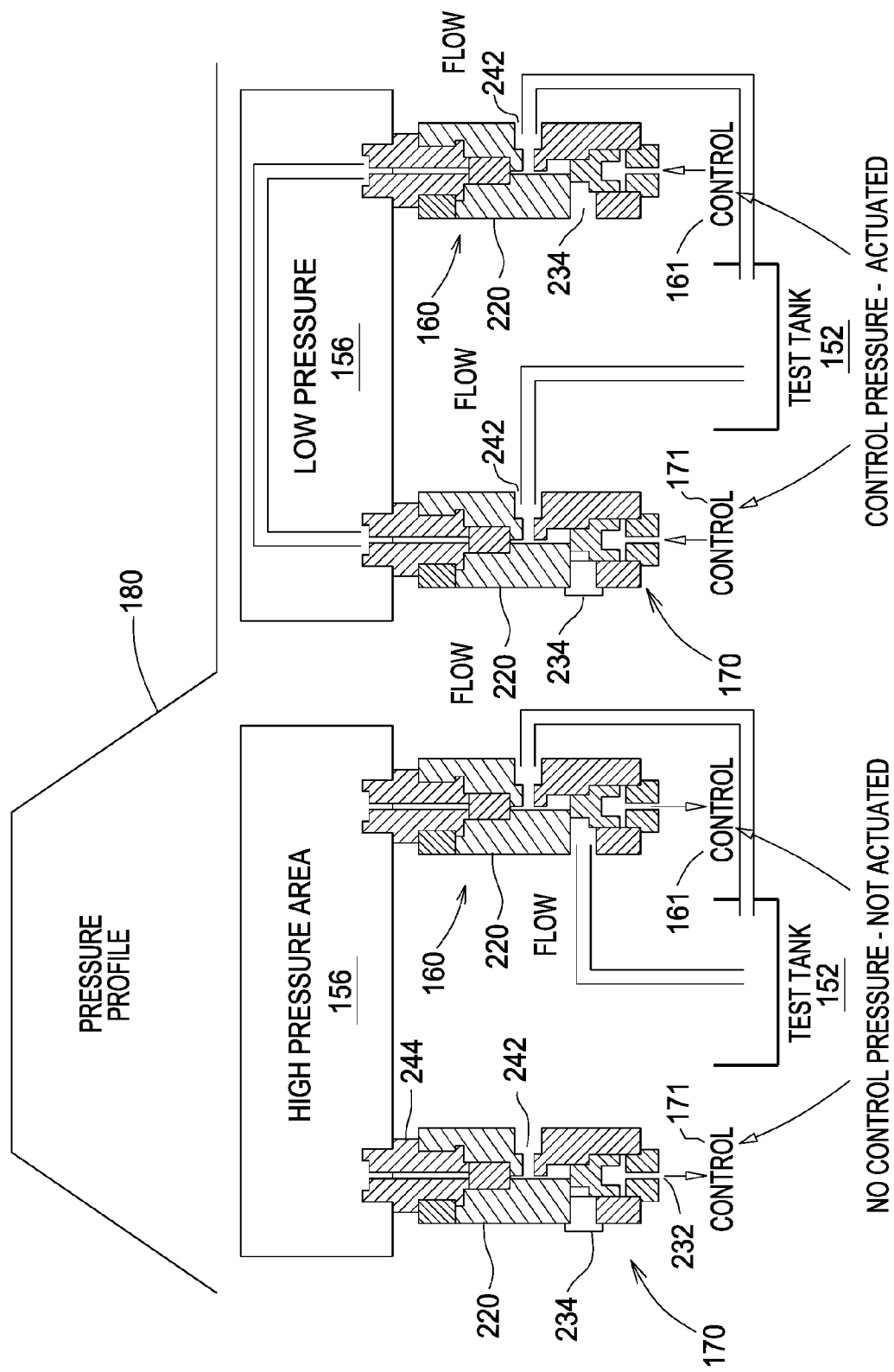
FIG. 3 is a cut away view of two high pressure and temperature valves, including operation, according to an embodiment.

FIG. 3 shows a cutaway view of two valves 160, and 170, during an operating cycle of system 100, according to an embodiment. As shown during high pressure portion of pressure profile 180, both valves 160 and 170 are not actuated. This no oil from the test tank to flow through valve 170, which is at the outlet of the hose test assemblies (from FIGS. 1 and 2). The high pressure area of the system is therefore isolated to allow pressure to increase and to be held in the high pressure area.

Also during the high pressure portion of the pressure wave 180, valve 160 is not actuated, which allows oil to circulate back through valve 160 to the test tank. The high pressure area of the system is therefore isolated to allow pressure to increase and to be held in the high pressure area.

During the low pressure portion of the pressure profile 180, valves 160 and 170 are actuated via control pressure. This changes the flow path of the oil. Valve 170 will then allow oil to flow through the test assembly back to the test tank, and allow pressure to decrease. Valve 160 will allow oil to flow from the test tank into the test assemblies.

Figure 4:
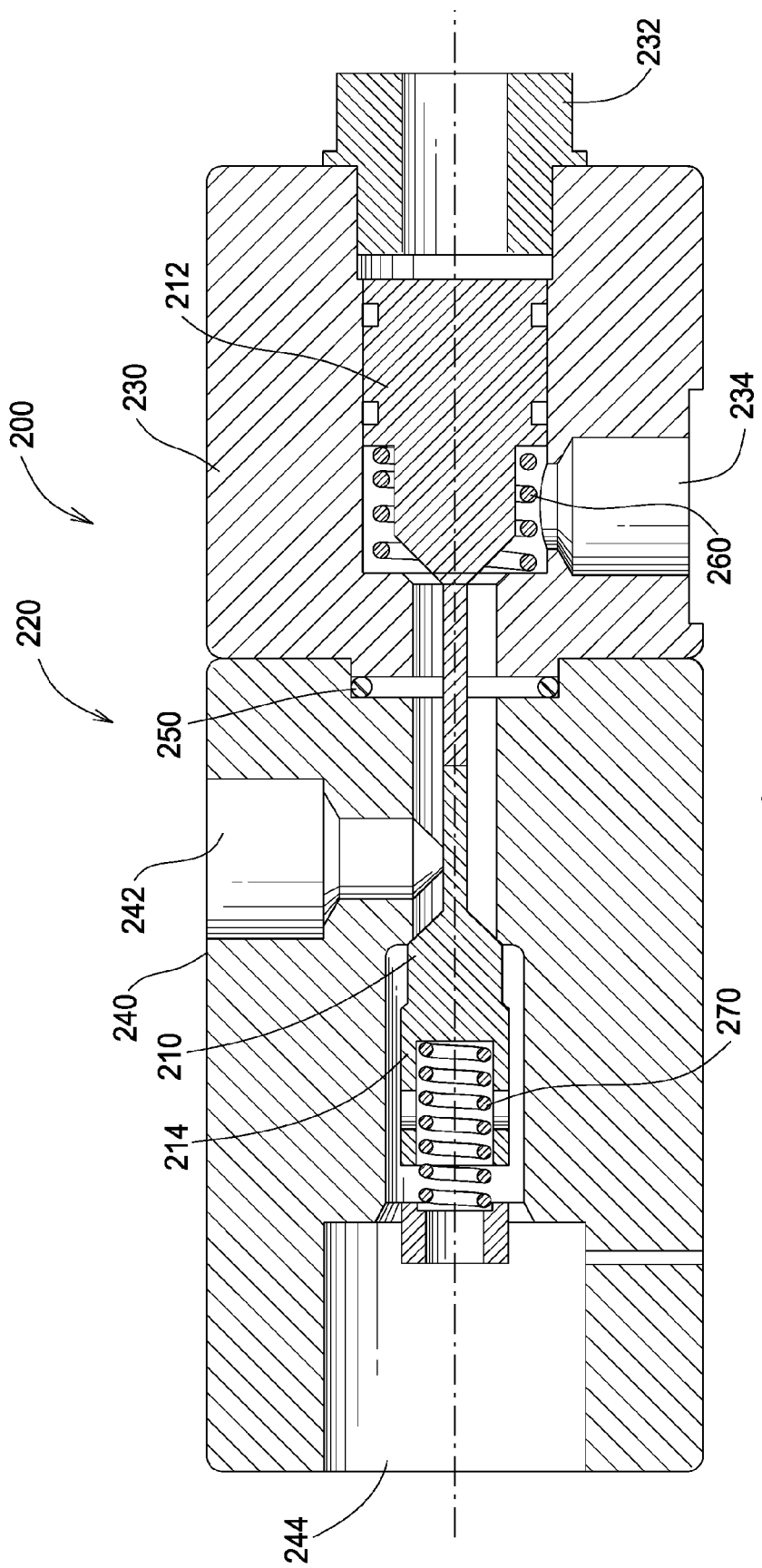
FIG. 4 is a cutaway view of a high pressure and temperature valve according to an embodiment.

FIG. 4 shows a cutaway view of the seal-less high pressure and temperature valve 200. Valve 200 may include a valve piston 210, a body 220, an assembly ring 250, a control biasing member 260 and return biasing member 270.

Body 220 may include a control portion 230 and a return portion 240. Control portion 230 may include an actuation orifice 232 capable of receiving actuation fluid and/or some other actuation signal to move valve piston 210 from an unactuated to an actuated position. As described in FIG. 3, the unactuated position isolates the test tank (not shown) from the test assembly (not shown) to allow intensifier (not shown) to increase pressure in the test assembly. In the unactuated position, fluid may flow into inlet 242 of return portion 240, and out of test tank outlet 234 of control portion 230 of body 220.

As shown in FIG. 3, valve 160 allows fluid to return to test tank. In the embodiment shown in FIG. 3, valve 170 does not have a connection to test tank outlet 234, and test tank outlet 234 may be capped or otherwise plugged and/or not used.

In the actuated position, valve piston 210 may allow fluid to flow into inlet 242 and out of assembly outlet 244. This may allow pressure to decrease and allow flow of fluid through the test assembly and back into test tank.

Valve piston 210 may be biased into the unactuated position by control biasing member 260 and return biasing member 270. Furthermore, valve piston 210 may include a control portion of piston 212 and return portion of piston 214. Piston may have two portions to make assembly and maintenance easier and more accessible.

In an embodiment, control portion 230 and return portion 240 may be bolted together. However, other methods, systems, and/or substances may be used to bond the parts of the system together without straying from the spirit and scope of this disclosure. Body 220 has two portions for assembly and maintenance purposes.

Valve 200 may be precision machined so as not to use valve seals. This may increase the amount of pressure and temperature the valve may withstand. This also may increase life cycle and decrease maintenance time and cost.

Valve body 220 and valve piston 210 may be formed from D2 high quality steel. It will be appreciated that other material suitable for this application may be used without straying from the spirit and scope of this disclosure.

Biasing members 260 and 270 may be formed from stainless steel to increase the life cycle of the biasing members, thereby decreasing maintenance time and costs.

According to embodiments, this configuration of valves 160, 170 and 200, may be able to function with fluid temperatures over 150 degrees Celsius, 700 bar of pressure, for over one million cycles of 1.0 seconds of over 700 bar pressure.

Oil may be HD 46 or any other suitable oil for this use and application.

Assembly ring 250 may be used as a seal between the two portions of body 220, but is not considered a valve seal in the ordinary sense of valve sealing.

Although the present disclosure and its advantages have been described in detail, it should be understood that various changes, substitutions, and alterations can be made herein without departing from the spirit and scope of the disclosure as defined by the appended claims. Moreover, the scope of the present application is not intended to be limited to the particular embodiments of the process, machine, manufacture, composition of matter, means, methods, and steps described in the specification. As one of ordinary skill in the art will readily appreciate from the disclosure of the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps. The disclosure disclosed herein may suitably be practiced in the absence of any element that is not specifically disclosed herein.

What is claimed is:

1. A valve comprising:
a valve body (220);
a first piston (210) fixedly connected to a second piston (212) within the valve body, the first piston and second piston disposed at opposite distal ends of the valve body;
a first biasing member (270) urging the first piston (210) closed and a second biasing member (260) simultaneously urging the second piston (212) open;
an inlet (242) in fluid communication with an outlet (234) when the first piston (210) is closed and the second piston (212) is open;
the second piston (212) is closed and the first piston (210) is open upon application of a fluid pressure sufficient to overcome the cumulative force of first biasing member (270) and the second biasing member (260) when the fluid pressure is applied to the second piston (212) through a fluid inlet (232); and
the first piston (210) when open causes a second inlet (244) to be in fluid communication with the inlet (242) and causes the second piston to close outlet (234).

2. The valve as in claim 1, wherein first biasing member (270) comprises a spring and second biasing member (260) comprises a spring.

3. The valve as in claim 1, wherein the second inlet (244) is not in fluid communication with inlet (242) or with outlet (234) when the first piston (210) is closed.

* * * * *